US004001712B2

United States Statutory Invention Registration [19]

[11] Reg. Number: H1712

Papalos et al.

[45] Published: Feb. 3, 1998

[54] RADIATION-CURABLE ACRYLATES OF POLYOL MONOALKYL ETHERS

[75] Inventors: John G. Papalos, Ledgewood; Joseph V. Sinka, Whitehouse Station, both of N.J.

[73] Assignee: Henkel Corporation, Plymouth Meeting, Pa.

[21] Appl. No.: 255,493

[22] Filed: Jun. 8, 1994

Related U.S. Application Data

[63] Continuation-in-part of Ser. No. 103,475, Aug. 6, 1993, abandoned.

[51] Int. Cl.[6] ..... C07C 69/52

[52] U.S. Cl. ..... 560/224

[56] References Cited

U.S. PATENT DOCUMENTS

| | | | |
|---|---|---|---|
| 4,256,910 | 3/1981 | Hsu | 560/224 |
| 4,876,384 | 10/1989 | Higbie et al. | 560/224 |
| 5,219,479 | 6/1993 | Mathieson | 560/224 |

FOREIGN PATENT DOCUMENTS

| | | |
|---|---|---|
| 9084884 | 5/1984 | Japan . |
| 1001642 | 1/1986 | Japan . |
| 3091350 | 4/1988 | Japan . |
| 4136041 | 5/1992 | Japan . |

*Primary Examiner*—Charles T. Jordan
*Assistant Examiner*—Meena Chelliah
*Attorney, Agent, or Firm*—Ernest G. Szoke; Wayne C. Jaeschke; J. Daniel Wood

[57] ABSTRACT

Radiation-curable compositions containing monoalkyl or mono-aralkyl ether di-acrylates or di-methacrylates of particular ethoxylated and/or propoxylated polyols of formulae I and II have been developed. These polyol derivatives substituted with hydrophobic ether functionalities constitute UV-curable diluents that can be isolated in excellent yields with minimal losses during the manufacturing process.

32 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

RADIATION-CURABLE ACRYLATES OF POLYOL MONOALKYL ETHERS

CROSS-REFERENCE TO RELATED APPLICATIONS

This application is a continuation-in-part of U.S. Ser. No. 08/103,475 filed Aug. 6, 1993, now abandoned Oct. 17, 1994 the disclosure of which is incorporated by reference herein.

BACKGROUND OF THE INVENTION

1. Field of the Invention

This invention relates to mono-alkyl or mono-aralkyl ether di-acrylates or di-methacrylates of particular ethoxylated and/or propoxylated polyols of general formulae I and II which are useful as diluents in radiation-curable compositions and to radiation-curable compositions containing same.

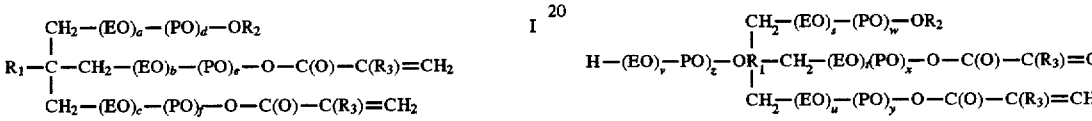

I

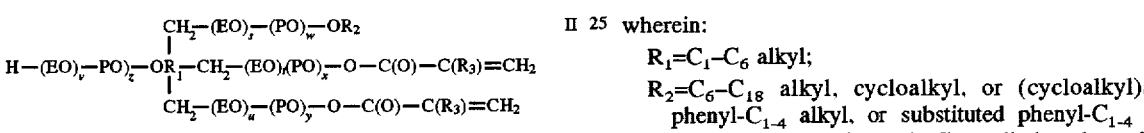

II

The compounds of the present invention exhibit distinct process advantages over the known corresponding monomethyl ethers.

2. Description of the Prior Art

Radiation curable or hardenable compositions, particularly for coating applications, are known in the art. Examples of reactive monomers, also referred to as radiation-curable diluents, are multi-functional acrylates and methacrylates of alkoxylated and non-alkoxylated poylols. Reference is made to the following United States patent and United States patents cited therein:

4,876,384 Higbie et al., Oct. 24, 1989

Among the more useful diluents disclosed in the '384 patent are the monomethyl ether acrylates and methacrylates of ethoxylated and/or propoxylated polyols. These compounds are characterized by their low viscosity and good solvation power and are thus utilized as viscosity enhancers in UV-curing formulations. However, these methyl ethers suffer from a commercially significant disadvantage of being obtainable in considerably reduced yields due to their relatively high water solubility. These losses (as much as 30%) take place during the extensive washing procedures which are used as part of the manufacturing process. As a consequence, there existed a need for related alkyl ether polyol acrylates having UV-curable properties analogous to those of the monomethyl ethers but which could be isolated without the losses associated with the methyl ethers. It is therefore an object of this invention to provide novel polyol acrylate diluents substituted with hydrophobic alkyl or aralkyl ether groups having that possess excellent UV-curing characteristics and which are isolable in essentially quantitative yields.

SUMMARY OF THE INVENTION

The UV-curable polyol monoalkyl ether acrylates of the present invention are the triol derivatives of general structural formula I:

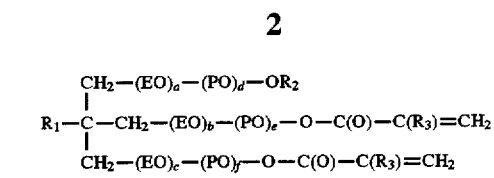

I wherein:

$R_1$=$C_2$–$C_9$ alkyl;

$R_2$=$C_6$–$C_{18}$ alkyl, cycloalkyl, or (cycloalkyl)alkyl, phenyl-$C_{1-4}$ alkyl, or substituted phenyl-$C_{1-4}$ alkyl, in which the substituent is $C_{1-4}$ alkyl at the ortho- or para-position of the phenyl ring;

EO=—$OCH_2CH_2$—;

PO=—$OCH_2CH_2CH_2$—;

a, b, c, d, e, and f each being an integer from 0–5, provided that the sum of a, b, c, d, e, and f=3–15; and $R_3$=H or $CH_3$ and the tetraol derivatives of general structural formula II:

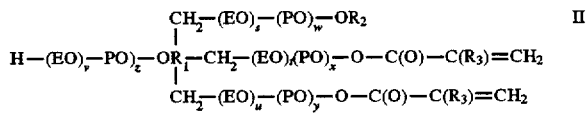

II wherein:

$R_1$=$C_1$–$C_6$ alkyl;

$R_2$=$C_6$–$C_{18}$ alkyl, cycloalkyl, or (cycloalkyl)alkyl, phenyl-$C_{1-4}$ alkyl, or substituted phenyl-$C_{1-4}$ alkyl, wherein the substituent is $C_{1-14}$ alkyl at the ortho- or para-position of the phenyl ring;

EO=—$OCH_2CH_2$—;

PO=—$OCH_2CH_2CH_2$—;

s, t, u, v, w, x, y, and z being integers from 0–5, provided the sum of s, t, u, v, w, x, y, and z=3–20; and $R_3$=H or $CH_3$.

DETAILED DESCRIPTION OF THE INVENTION

The invention encompasses novel mono-O-alkyl or mono-O-aralkyl ether diacrylates of particular ethoxylated and/or propoxylated polyols of formulae I and II useful as diluents for radiation-curable compositions. These polyol derivatives have been discovered to exhibit distinct process advantages over the corresponding previously described monomethyl ethers. Replacing the methyl ether group with a more hydrophobic ether group, such as benzyl, cinnamyl, and nonyl, provides compounds with low-viscosity and good solvation power and which are particularly compatible with the other ingredients of relatively hydrophobic coating formulations. Such compatibility can improve the uniformity of films prepared from such coating formulations. Moreover, the more hydrophobic diluents are isolated in very high yields (99%) with minimal losses observed during the manufacturing process compared with the methyl ethers. The compounds of the present invention cure at a faster rate than the methyl ethers when they are subjected to ultraviolet radiation. Overall, the claimed diluents display uniquely fast curing and formulation properties, features highly desirable in the UV-curing practice.

Since the solvation strength and film properties are attributed to the diacrylate functionalities in these compounds, the core backbone has a polyol structure with three or four free hydroxyl groups, two being available for acrylation and one for etherification with a hydrophobic alkyl or aralkyl halide. The UV-curable diluents are consequently restricted to triol monoether diacrylates of formula I

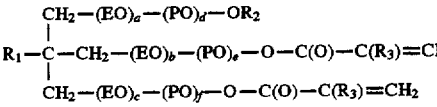

I wherein:

$R_1$=$C_2$–$C_9$ alkyl;

$R_2$=$C_6$–$C_{18}$ alkyl, cycloalkyl, or (cycloalkyl)alkyl, phenyl-$C_{1-4}$ alkyl, or substituted phenyl-$C_{1-4}$ alkyl, in which the substituent is $C_{1-14}$ alkyl at the ortho- or para-position of the phenyl ring;

EO=—$OCH_2CH_2$—;

PO=—$OCH_2CH_2CH_2$—;

a, b, c, d, e, and f each being an integer from 0–5, provided that the sum of a, b, c, d, e, and f=3–15; and $R_3$=H or $CH_3$ and tetraol monoether diacrylates of formula II

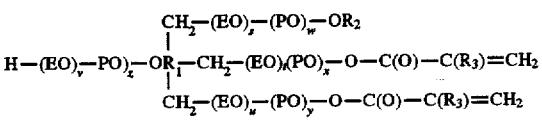

II wherein:

$R_1$=$C_1$–$C_6$ alkyl;

$R_2$=$C_6$–$C_{18}$ alkyl, cycloalkyl, or (cycloalkyl)alkyl, phenyl-$C_{1-4}$ alkyl, or substituted phenyl-$C_{1-4}$ alkyl, wherein the substituent is $C_{1-14}$ alkyl at the ortho- or para-position of the phenyl ring;

EO=—$OCH_2CH_2$—;

PO=—$OCH_2CH_2CH_2$—;

s, t, u, v, w, x, y, and z being integers from 0–5, provided the sum of s, t, u, v, w, x, y, and z=3–20; and $R_3$=H or $CH_3$.

One genus of this embodiment comprises compounds of the formula I wherein:

$R_1$=$C_2$–$C_9$ alkyl; and $R_2$=$C_6$–$C_{14}$ alkyl, cycloalkyl, or cycloalkylmethyl, or phenyl-$C_{1-2}$ alkyl.

One class of this genus is the compounds wherein:

$R_1$=$CH_3CH_2$.

A sub-class of this class is the compounds wherein:

$R_1$=$CH_3CH_2$; and $R_2$=$C_{6-14}$ and alkyl or phenyl-$C_{1-2}$ alkyl.

A second genus of this embodiment comprises compounds of the formula II wherein:

$R_1$=$C_1$–$C_6$ alkyl; and $R_2$=$C_{6-14}$ alkyl, cycloalkyl, or cycloalkylmethyl, or phenyl-$C_{1-2}$ alkyl.

One class of this second genus is the compounds wherein:

$R_1$=$C_1$

A sub-class of this class is the compounds wherein:

$R_1$=$C_1$; and $R_2$=$C_{6-14}$ alkyl or phenyl-$C_{1-2}$ alkyl.

In each of formulas I and II, $R_2$ preferably has at least seven carbon atoms (e.g. $C_7$ alkyl) and more preferably has 12 to 16 carbon atoms (e.g. is $C_{12-16}$ alkyl).

It should also be noted that while the subscripts a, b, c, d, e, and f are each integers for a pure compound of formula I and the subscripts s, t, u, v, w, x, y, and z are integers for a pure compound of formula II, a mixture of more than one compound of formula I or more than one compound of formula II can be represented by non-integer values for these subscripts (i.e. the non-integer value being the average of each subscript value for each compound in the mixture). Because of the mechanism of the ethoxylation and propoxylation reactions, the product of an ethoxylation or propoxylation of trimethylolpropane or pentaerythritol, particularly where a low degree of ethoxylation or propoxylation is accomplished (e.g. a triethoxylation), will be comprised predominantly of compounds wherein the subscripts a, b, c, d, e, and f or s, t, u, v, w, x, y, and z each will be equal or will deviate by only unity (one). In the list below, the term "tri-ethoxylated" means that the compound will contain a total of three ethyleneoxy groups.

Exemplifying the invention are the following compounds:

(a) mono-O-hexyl tri-ethoxylated trimethylolpropane diacrylate;

(b) mono-O-nonyl tri-ethoxylated trimethylolpropane diacrylate;

(c) mono-O-decyl tri-ethoxylated trimethylolpropane diacrylate;

(d) mono-O-dodecyl tri-ethoxylated trimethylolpropane diacrylate;

(e) mono-O-tetradecyl tri-ethoxylated trimethylolpropane diacrylate;

(f) mono-O-benzyl tri-ethoxylated trimethylolpropane diacrylate;

(g) mono-O-cinnamyl tri-ethoxylated trimethylolpropane diacrylate;

(h) mono-O-hexyl tri-ethoxylated pentaerythrityl diacrylate;

(i) mono-O-nonyl tri-ethoxylated pentaerythrityl diacrylate;

(j) mono-O-decyl tri-ethoxylated pentaerythrityl diacrylate;

(k) mono-O-dodecyl tri-ethoxylated pentaerythrityl diacrylate;

(l) mono-O-tetradecyl tri-ethoxylated pentaerythrityl diacrylate;

(m) mono-O-benzyl tri-ethoxylated pentaerythrityl diacrylate; and (n) mono-O-cinnamyl tri-ethoxylated pentaerythrityl diacrylate.

The compounds of the present invention are prepared as illustrated in Scheme I for the preparation of mono-O-benzyl-tri-ethoxylated trimethylolpropane diacrylate. The ethoxylated/propoxylated polyols, as represented by structure 1, are treated with aqueous base, such as 45% potassium hydroxide, at elevated temperatures, with azeotropic removal of water, to generate the corresponding alkoxides, as represented by structure 2. The alkoxides are then reacted with the appropriate alkyl halide or aralkyl halide to afford the corresponding mono-O-alkyl ethoxylated/propoxylated polyols, as represented by structure 3. The later polyol ethers are then converted into their di-acrylates or di-methacrylates, as represented by structure 4, by reaction with acrylic acid or methacrylic acid, respectively, in the presence of cuprous oxide and an acid catalysts, such as p-toluenesulfonic acid or methanesulfonic acid, with azeotropically removal of water. Acrylation or methacrylation may also be effected under Schotten-Bauman conditions using acryloyl chloride or methacryloyl chloride, respectively.

a) monoalkoxide of tri-ethoxylated trimethylolpropane

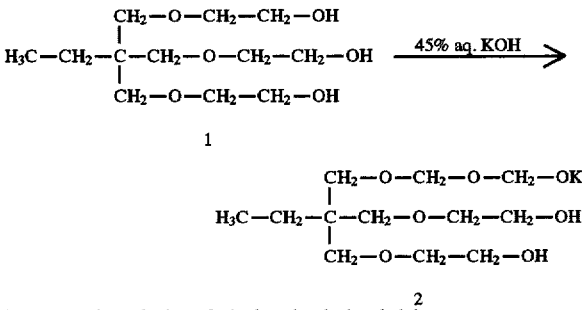

1

2 b) mono-O-benzyl ether of tri-ethoxylated trimethylolpropane

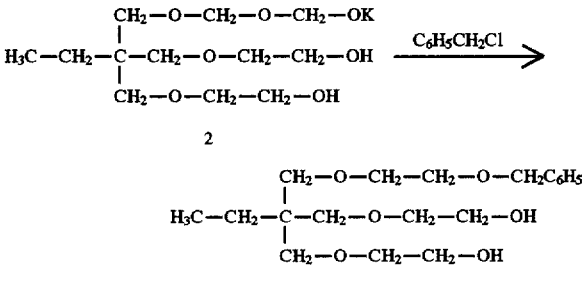

2

3 c) mono-O-benzyl ether of tri-ethoxylated trimethylolpropane diacrylate

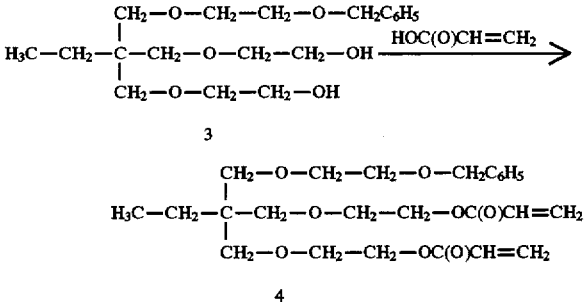

3

4

For a fuller understanding of the invention, reference may be made to the following examples. These examples are intended to illustrate the preparation of the polyol ether derivatives of the present invention and as such are not intended to limit the invention as set forth in the claims appended thereto.

EXAMPLE 1

Preparation of mono-O-benzyl tri-ethoxylated trimethylolpropane

A 250 mL flask, equipped to conduct an azeotropic distillation, was charged with tri-ethoxylated trimethylolpropane (50.0 g, 0.2 mol), toluene (50 g), and 45% aqueous potassium hydroxide (12.5 g, 0.1 mol). The reaction mixture was heated under a nitrogen atmosphere (105°–112° C.) with azeotropic removal of water. The process was continued until no more water collected in the receiver. The reaction was then cooled to 70° C. and benzyl chloride (12.7 g) was added. The mixture was heated at 90°–95° C. for three hours. Another 12.5 g of 45% potassium hydroxide was added at 70° C., and heating was continued at 105°–112° C. to effect azeotropic removal of water. After cooling to 70° C., another 12.7 g of benzyl chloride was added, followed by heating at 90°–95° C. for a further three hours. Distilled water (27 g) was then added, and the reaction mixture was stirred for thirty minutes. The mixture was transferred to a separatory funnel and the layers allowed to separate. The lower layer was discarded, and the upper layer was evaporated under diminished pressure to remove toluene. The resulting product was filtered to afford the title compound having a hydroxyl number of 341 (99% of theoretical value).

EXAMPLE 2

Preparation of mono-O-cinnamyl tri-ethoxylated trimethylolpropane

The title compound was prepared in analogous fashion as Example 1, except that the benzyl chloride was substituted with cinnamyl bromide. The resulting mono-cinnamyl ether had a hydroxyl number of 309 (about 100% of the theoretical value).

EXAMPLE 3

Preparation of mono-O-nonyl tri-ethoxylated trimethylolpropane

The title compound was prepared in analogous fashion as Example 1, except that the benzyl chloride was substituted with nonyl iodide. The resulting mono-nonyl ether had a hydroxyl number of 292 (about 98% of the theoretical value).

EXAMPLE 4

Preparation of mono-O-cyclohexylmethyl tri-ethoxylated trimethylolpropane

The title compound was prepared in an analogous fashion as Example 1, except that the benzyl chloride was substituted with cyclohexylmethyl bromide. The resulting mono-cyclohexylmethyl ether had a hydroxyl number of 382 (about 80 of the theoretical value).

EXAMPLE 5

Preparation of mono-O-hexyl tri-ethoxylated trimethylolpropane

The title compound was prepared in an analogous fashion as Example 1, except that the benzyl chloride was substituted with hexyl chloride. The resulting mono-hexyl ether had a hydroxyl number of 330 (about 98% of the theoretical value).

EXAMPLE 6

Preparation of mono-O-benzyl tri-ethoxylated trimethylolpropane diacrylate

A 500 mL reaction flask, equipped for azeotropic distillation, was charged with 164.3 g (one equivalent) of the monobenzyl ether of Example 1, 85.6 g of toluene, 0.17 g of cuprous oxide, 8.06 g of p-toluenesulfonic acid, and 75.6 g of acrylic acid (1.05 equivalent). The reaction mixture was heated at 95°–100° C. with azeotropic removal of water until the acid value was reduced to about 17.0. The resulting diacrylate was washed with a solution containing 8% sodium chloride, 3% sodium hydrogen carbonate, and 0.002% ethylenediamine tetraacetic acid. The layers were then separated, the toluene removed by evaporation under diminished pressure, and the final product filtered. The resulting monobenzyl diacrylate had an AV of 0.3 Me/g and free hydroxyl of 36, which represents about 96% acrylylation of the free hydroxyls.

EXAMPLE 7

Radiation-curing of mono-O-alkyl tri-ethoxylated trimethylolpropane diacrylates

Into an aluminum dish there was mixed 92 parts of the mono-O-alkyl tri-ethoxylated trimethylolpropane diacrylate, 6.0 g of benzophenone, and 2.0 g of triethanolamine. The liquid was drawn down to about a 0.27 mils (6.86 micrometers) thick film with a #3 RDS Rod on a glass panel. The film was cured on the panel by passing, under a 300 watt/inch bulb, UV radiation at 100 ft/min until the film on the panel was tack-free. Using this procedure, the following data were obtained:

Cured-film Properties of mono-O-alkyl tri-ethoxylated trimethylolpropane diacrylate

| Diacrylate | Cured Film Properties | | | | | | |
|---|---|---|---|---|---|---|---|
| Monoether | Cure | Scuff | Gloss | Pencil | MEK | ADHS | Mandrel |
| Methyl | 8 | G | G | 6H | 13 | O | <0.25 |
| Example 6 | 3 | G | G | 4H | 5 | O | <0.25 |

1# Number of passes to tack-free curing

What is claimed is:

1. A compound of formula I

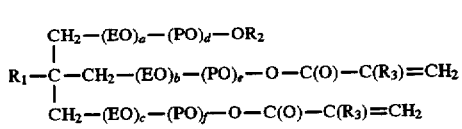

I wherein:

$R_1=C_2-C_9$ alkyl;

$R_2=C_6-C_{18}$ alkyl, cycloalkyl, or (cycloalkyl)alkyl, phenyl-$C_{1-4}$ alkyl, or substituted phenyl-$C_{1-4}$ alkyl, in which the substituent is $C_{1-4}$ alkyl at the ortho- or para-position of the phenyl ring;

$EO=OCH_2CH_2$—;

$PO=OCH_2CH_2CH_2$—;

a, b, c, d, e, and f each being an integer from 0–5, provided that the sum of a, b, c, d, e, and f=3–15; and $R_3$=H or $CH_3$.

2. A compound according to claim 1 wherein $R_1=C_2-C_9$ alkyl and $R_2=C_{6-14}$ alkyl, cycloalkyl, or cycloalkylmethyl, or phenyl-$C_{1-2}$ alkyl.

3. A compound according to claim 2 wherein $R_1=CH_3CH_2$.

4. A compound according to claim 2 wherein $R_1=CH_3CH_2$ and $R_2=C_{6-14}$ alkyl or phenyl-$C_{1-2}$ alkyl.

5. A compound according to claim 4 wherein the sum of a, b, c, d, e, and f is 3.

6. A compound according to claim 1 which is mono-O-hexyl tri-ethoxylated trimethylolpropane diacrylate.

7. A compound according to claim 1 which is mono-O-nonyl tri-ethoxylated trimethylolpropane diacrylate.

8. A compound according to claim 1 which is mono-O-decyl tri-ethoxylated trimethylolpropane diacrylate.

9. A compound according to claim 1 which is mono-O-dodecyl tri-ethoxylated trimethylolpropane diacrylate.

10. A compound according to claim 1 which is mono-O-tetradecyl tri-ethoxylated trimethylolpropane diacrylate.

11. A compound according to claim 1 which is mono-O-benzyl tri-ethoxylated trimethylolpropane diacrylate.

12. A compound according to claim 1 which is mono-O-cinnamyl tri-ethoxylated trimethylolpropane diacrylate.

13. A compound according to claim 1 wherein $R_2$ has at least seven carbon atoms.

14. A compound according to claim 1 wherein $R_2$ is $C_7-C_{14}$ alkyl, cycloalkyl, or (cycloalkyl)alkyl, phenyl-$C_{1-4}$ alkyl, or substituted phenyl-$C_{1-4}$ alkyl, in which the substituent is $C_{1-14}$ alkyl at the ortho- or para-position of the phenyl ring.

15. A compound of claim 1 wherein $R_2$ is $C_{12}-C_{16}$ alkyl, cycloalkyl, or (cycloalkyl)alkyl, phenyl-$C_{1-4}$ alkyl, or substituted phenyl-$C_{1-4}$ alkyl, in which the substituent is $C_{1-4}$ alkyl at the ortho- or para-position of the phenyl ring.

16. A compound of claim 15 wherein the each of a, b, and c is one and d, e, and f, are zero.

17. A compound of formula II

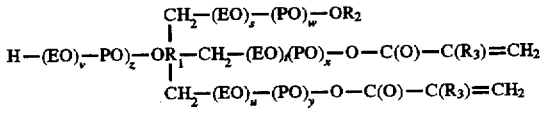

II wherein:

$R_1=C_1-C_6$ alkyl;

$R_2=C_6-C_{18}$ alkyl, cycloalkyl, or (cycloalkyl)alkyl, phenyl-$C_{1-4}$ alkyl, or substituted phenyl-$C_{1-4}$ alkyl, wherein the substituent is $C_{1-14}$ alkyl at the ortho- or para-position of the phenyl ring;

$EO=OCH_2CH_2$—;

$PO=OCH_2CH_2CH_2$—;

s, t, u, v, w, x, y, and z being integers from 0–5, provided the sum of s, t, u, v, w, x, y, and z=3–20; and $R_3$=H or $CH_3$.

18. A compound according to claim 17 wherein $R_1=C_{1-6}$ alkyl; and $R_2=C_{6-14}$ alkyl, cycloalkylmethyl, or phenyl-$C_{1-2}$ alkyl.

19. A compound according to claim 18 wherein $R_1=C_1$.

20. A compound according to claim 18 wherein $R_1=C_1$ and $R_2=C_{6-14}$ alkyl or phenyl-$C_{1-2}$ alkyl.

21. A compound according to claim 20 wherein the sum of s, t, u, v, w, x, y, and z is 3.

22. A compound according to claim 17 which is mono-O-hexyl tri-ethoxylated pentaerythrityl diacrylate.

23. A compound according to claim 17 which is mono-O-nonyl tri-ethoxylated pentaerythrityl diacrylate.

24. A compound according to claim 17 which is mono-O-decyl tri-ethoxylated pentaerythrityl diacrylate.

25. A compound according to claim 17 which is mono-O-dodecyl tri-ethoxylated pentaerythrityl diacrylate.

26. A compound according to claim 17 which is mono-O-tetradecyl tri-ethoxylated pentaerythrityl diacrylate.

27. A compound according to claim 17 which is mono-O-benzyl tri-ethoxylated pentaerythrityl diacrylate.

28. A compound according to claim 17 which is mono-O-cinnamyl tri-ethoxylated pentaerythrityl diacrylate.

29. A compound according to claim 17 wherein $R_2$ has at least seven carbon atoms.

30. A compound according to claim 17 wherein $R_2$ is $C_7-C_{14}$ alkyl, cycloalkyl, or (cycloalkyl)alkyl, phenyl-$C_{1-4}$ alkyl, or substituted phenyl-$C_{1-4}$ alkyl, in which the substituent is $C_{1-14}$ alkyl at the ortho- or para-position of the phenyl ring.

31. A compound of claim 17 wherein $R_2$ is $C_{12}-C_{16}$ alkyl, cycloalkyl, or (cycloalkyl)alkyl, phenyl-$C_{1-4}$ alkyl, or substituted phenyl-$C_{1-4}$ alkyl, in which the substituent is $C_{1-14}$ alkyl at the ortho- or para-position of the phenyl ring.

32. A compound according to claim 31 wherein the sum of s, t, u, and v is 3 and each of v, w, x, y, and z is zero.

* * * * *